United States Patent
Matloub et al.

(10) Patent No.: US 7,678,092 B2
(45) Date of Patent: Mar. 16, 2010

(54) COLLAPSIBLE FLUID CONTAINMENT DEVICE WITH SEMI-RIGID SUPPORT MEMBERS

(76) Inventors: Haitham Matloub, N8W28814 Shepherds Way, Waukesha, WI (US) 53188; Brenda Matloub, N8W28814 Shepherds Way, Waukesha, WI (US) 53188; Philip Narini, 117 King Street East, Oshawa, Ontario (CA) L1H 1B9

( * ) Notice: Subject to any disclaimer, the term of this patent is extended or adjusted under 35 U.S.C. 154(b) by 90 days.

(21) Appl. No.: 11/684,509

(22) Filed: Mar. 9, 2007

(65) Prior Publication Data

US 2008/0219642 A1    Sep. 11, 2008

(51) Int. Cl.
  *A61F 5/44* (2006.01)
  *A61B 19/00* (2006.01)
  *A61B 19/08* (2006.01)
  *A61M 1/00* (2006.01)

(52) U.S. Cl. ............... 604/355; 604/408; 604/327; 128/855; 128/856

(58) Field of Classification Search ............ 604/289, 604/290, 327, 408, 355; 383/95, 33, 34, 383/35, 36; 137/590; 128/849, 853, 854, 128/855, 856
See application file for complete search history.

(56) References Cited

U.S. PATENT DOCUMENTS

| | | | |
|---|---|---|---|
| 3,788,369 A | | 1/1974 | Killinger |
| 3,850,172 A | | 11/1974 | Cazalis |
| 3,993,080 A | * | 11/1976 | Loseff ............ 604/28 |
| 4,000,749 A | | 1/1977 | Busco |
| 4,306,557 A | * | 12/1981 | North ............ 604/119 |
| 4,489,720 A | | 12/1984 | Morris et al. |
| 4,602,773 A | | 7/1986 | Craven, Jr. |
| 4,656,997 A | | 4/1987 | Morales-George |
| 5,107,859 A | | 4/1992 | Alcorn et al. |
| 5,178,162 A | | 1/1993 | Bose |
| 5,312,385 A | | 5/1994 | Greco |
| 5,316,541 A | | 5/1994 | Fischer |
| 5,335,618 A | * | 8/1994 | Zarola ............ 119/498 |
| 5,437,602 A | | 8/1995 | Polyakov et al. |
| 5,447,504 A | * | 9/1995 | Baker et al. ............ 604/289 |
| 5,743,435 A | | 4/1998 | Tomic |
| 5,970,979 A | | 10/1999 | Christofel et al. |
| 6,083,209 A | | 7/2000 | Marasco, Jr. |
| 6,217,507 B1 | | 4/2001 | Bonvik |
| 6,314,958 B1 | | 11/2001 | Harroll et al. |
| 6,461,290 B1 | * | 10/2002 | Reichman et al. ........ 600/21 |
| 2002/0148857 A1 | | 10/2002 | Savage et al. |
| 2004/0045557 A1 | | 3/2004 | Lee et al. |
| 2004/0073157 A1 | * | 4/2004 | Knudson et al. ........ 604/8 |
| 2006/0293630 A1 | * | 12/2006 | Manna et al. .......... 604/327 |

OTHER PUBLICATIONS

US 5,608,163, 03/1997, Beard (withdrawn)

* cited by examiner

*Primary Examiner*—John Rivell
*Assistant Examiner*—Atif H Chaudry
(74) *Attorney, Agent, or Firm*—Vedder Price P.C.; W. Dennis Drehkoff

(57) ABSTRACT

A collapsible fluid containment bag for irrigating and cleaning wounds on extremities having semi-rigid support members and an elevated lower support member attached to the bottom of the proximal end of the containment bag creating a gradient for allowing irrigation fluids and biological tissue to drain to the distal end of the bag for removal. The containment bag is collapsible, making it a convenient size for storage, transport, and disposal.

6 Claims, 4 Drawing Sheets

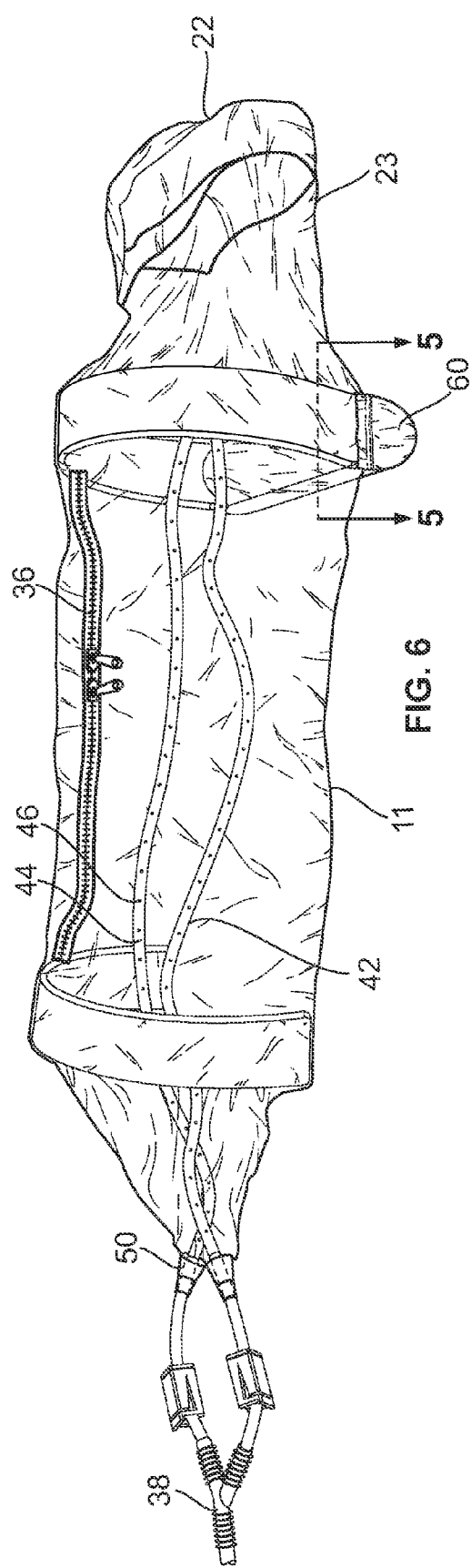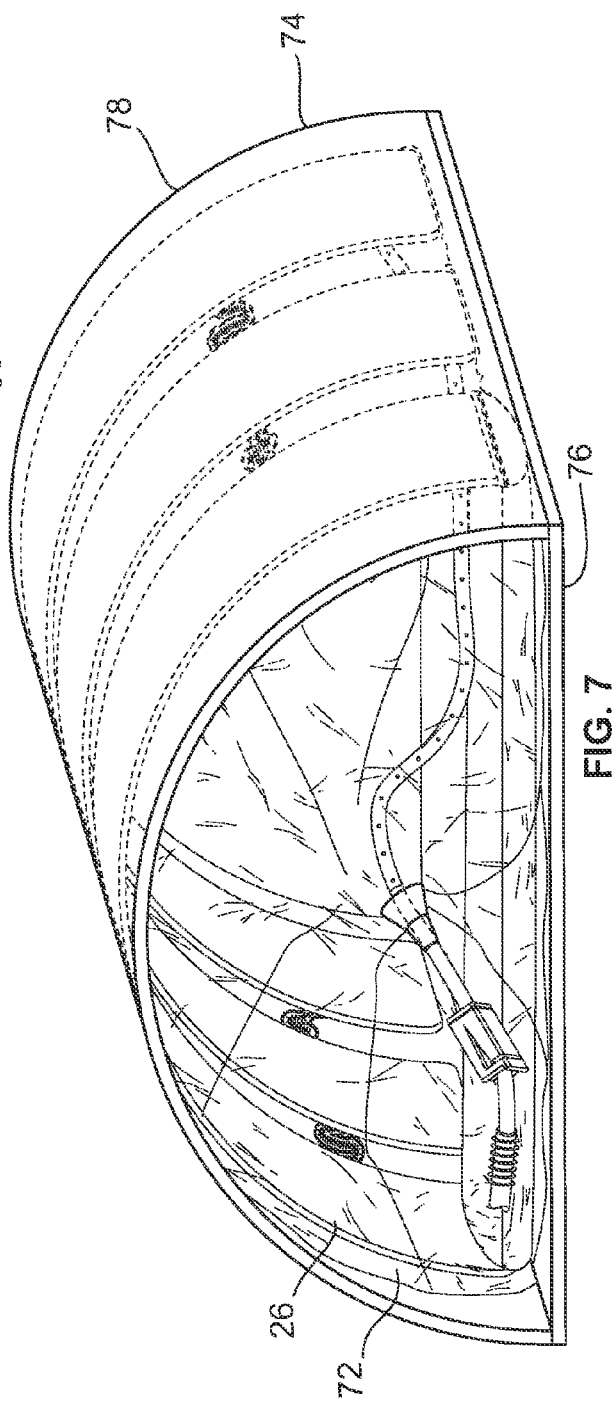

US 7,678,092 B2

COLLAPSIBLE FLUID CONTAINMENT DEVICE WITH SEMI-RIGID SUPPORT MEMBERS

FIELD OF THE DISCLOSURE

The invention relates generally to a wound irrigation/fluid containment system that isolates a wound on a person on which wound treatment is to be performed.

BACKGROUND

The cleaning and washing of wounds is required to remove foreign material and to decrease bacterial contamination. The wound-care provider, whether a first responder, nurse, physician, surgeon, or assistants, should be protected or isolated from bodily fluids and any contaminated irrigation fluids.

A collection pan or receptacle is usually placed under the wound that is to be treated in order to collect the irrigation fluid used during the irrigation and debridement. Debridement is the removal of foreign matter such as dirt, contaminates, or dead tissue. Irrigation is the flushing of fluid over the wound to remove smaller particles and bacteria to decrease the possibility of infection.

During irrigation and debridement procedures, often times the fluid is not received in a collection pan. Further, fluid can splash onto the wound-care provider, equipment, and surroundings. In other words, the collection pan placed under the wound usually does not catch all of the irrigation or wound fluids that are present during the irrigation and debridement procedure. This is of particular concern should the patient have blood-borne infections such as HIV, hepatitis, or cytomegalovirus, thereby putting the wound-care provider at risk of contracting an infectious disease. There are times when a patient may not be aware that they have contracted an infectious disease, and hence, the adoption of universal precautions has been recommended. The spillage of contaminated irrigation fluid requires sterilization of the materials in the immediate environment, which could include carpeting, walls, bed coverings, etc.

Therefore, there is a need for a fluid containment system that provides a barrier to the wound-care provider to the splash or spillage of contaminated irrigation fluids or body fluids. This system must contain and collect body and irrigation fluids. It must enclose them for the safety of the wound-care provider and provide adequate means for removing the irrigation fluids and biological tissue without restricting the activities of the wound-care provider. An additional need is evident for a containment device that can be reduced to a convenient size for storage, transport, and disposal.

DESCRIPTION OF THE PRIOR ART

U.S. Pat. No. 5,312,385 describes a collapsible enclosure for covering a limb for providing pulse irrigation to a wound thereon. An enclosure with inflatable ribbing, at least one outlet port, one opening for insertion of a body part, and an opening in the enclosure for providing access for a pulse irrigation nozzle is disclosed.

U.S. Pat. No. 5,316,541 describes a disposable, collapsible tent with a support structure for supporting the tent and an adhesive means for securing the tent to the patient's body. Gloves are formed from the wall of the tent so a surgeon may place his hands therein for manipulating surgical instruments and performing surgical procedures on the patient. A surgeon can operate on the patient by making an incision through the enclosure via use of the assembly on the patient's skin. The incision in the patient's body fluids is contained within the isolated cavity defined by the enclosure.

U.S. Pat. No. 5,608,163 describes a metal basin including a grid for supporting a limb enclosed in a free-standing transparent plastic enclosure. The basin collects irrigation fluids that are dispensed by a care giver whose hands are inserted through apertures in the side walls of the enclosure. The irrigation fluids are collected in the bottom of the basin for disposal.

U.S. Pat. No. 5,178,162 describes a fluid containment device that attempts to isolate an extremity of the body and provide drainage means for fluids used during irrigation and to allow access to the extremity by the surgeon to perform various functions.

U.S. Pat. No. 5,437,602 describes a fluid containment device using fenestrations or access ports for the surgeon that have apertures for inserting nozzles and another resealable opening for access to the extremity being treated. Removal of irrigation fluids is accomplished by manipulating a drainage plug in the bottom of the device. Vacuuming is required to remove the irrigation fluids, which would affect the collapse of the containment device.

It is desirable to provide a containment device for applying irrigation fluids and for debridement treatment that allows for the efficient drainage of the fluid or tissue to a drainage area for removal while providing protection to a wound-care provider.

SUMMARY OF THE INVENTION

The present invention describes a collapsible fluid containment device allowing for isolation of those in the vicinity of the irrigation of a patient or debridement of wound tissue on a patient from contaminated irrigation fluid or tissue. Generally, the collapsible fluid containment device of the present invention includes a flexible bag body for defining a containment space, the bag body comprising a wall having a proximal end, a distal end, and a drainage area at the distal end, the wall including semi-rigid structural support members and an elevated lower support member positioned under the proximal end to create a gradient so that fluids and dislodged biological matter will migrate by gravity to the drainage area at the distal end for removal and disposal.

BRIEF DESCRIPTION OF THE DRAWINGS

The invention will now be described by way of example only with reference to the following drawings:

FIG. 6 is a side view of another embodiment of a fluid containment device showing a single collection tube for receiving irrigation fluid, thereby allowing the fluid to drain from the containment device.

FIG. 7 is a perspective view of a folded or collapsed fluid containment device placed in a package for storage and/or transport.

DETAILED DESCRIPTION

Figure 1:
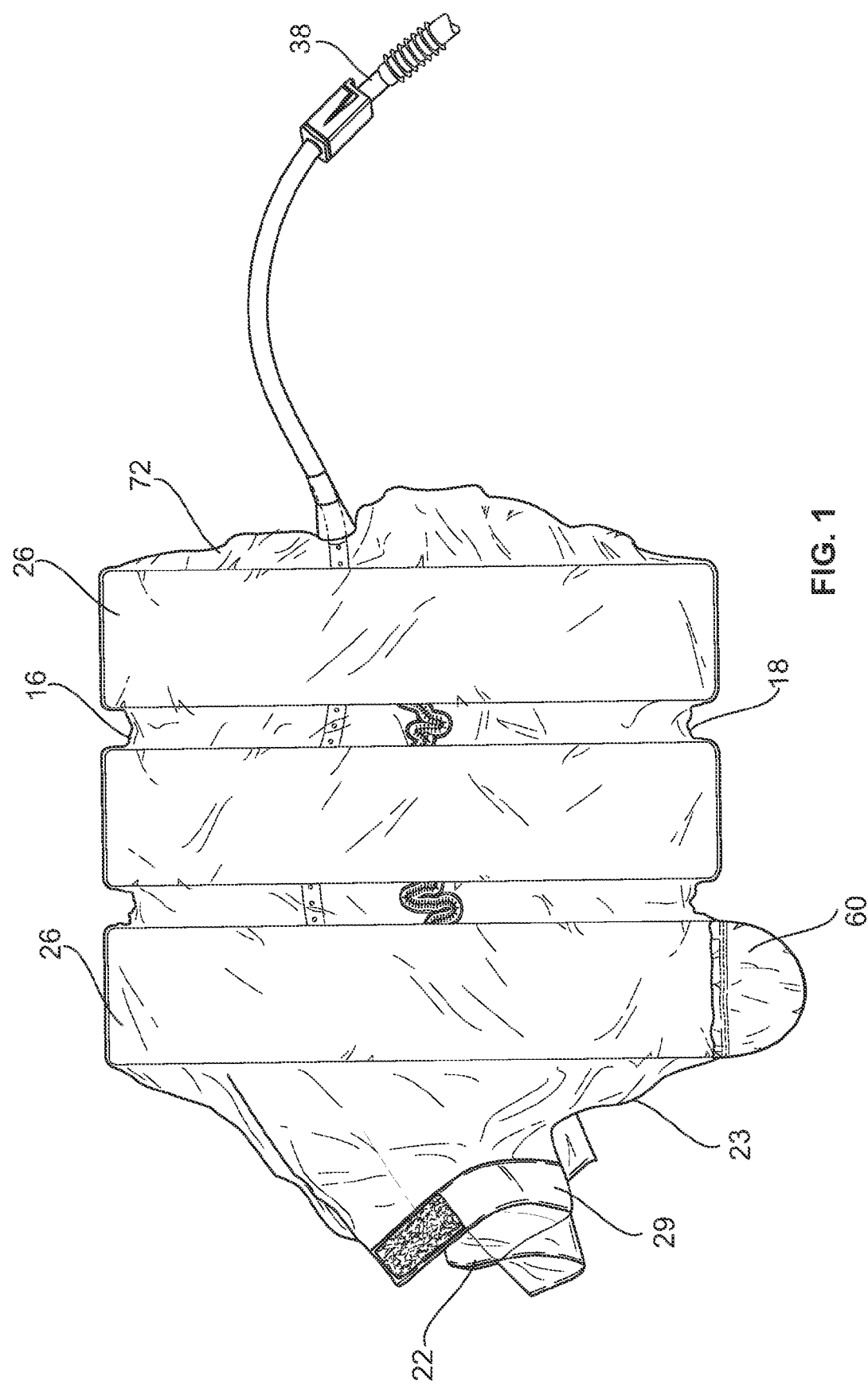
FIG. 1 is a side view of a fluid containment device in a folded position for storage or disposal.

Referring now to FIGS. 1-7, the present invention is a fluid containment device 10 illustrated in the figures and including the following components, namely, bag body 12, having a lower section 14 and an upper section 16. The fluid containment device 10 includes bottom 18 and continuous wall 20. The fluid containment device 10 can be made from one-piece clear plastic, such as polyvinylchloride, or can be manufactured from multiple pieces, including a separate floor, sidewalls, and top. The bottom and sidewalls define a proximal opening 22 in which a patient's limb may be inserted for care and treatment at proximal end 23. Distal portion 24 defines an area where tubing, hosing, or other means enter bag body 12 for removal of irrigation fluids and biological tissue from drainage area 25.

Figure 4:
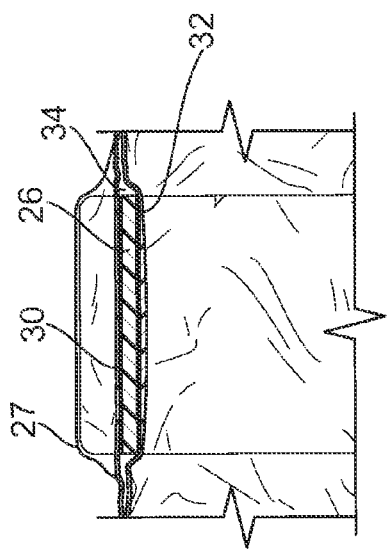
FIG. 4 is a cross-sectional view of a fluid containment device taken along lines 4-4 of FIG. 3.

The shape of the fluid containment device 10 is maintained with flexible, semi-rigid supports 26, which support the bag body and fluid containment device so that the patient's limb may be inserted therein. The flexible support members define containment space 28, which can receive the patient's limb for irrigation, wound treatment, debridement, or subsequent surgical procedures. Semi-rigid flexible structural support member 26 may engage fluid containment device 10 in any practical or conventional manner. However, it is preferred that the walls 20 and the lower section 14 and the upper section 16 of bag body 12 contain a double-wall sleeve 27 defining an opening for insertion of the flexible support member 26. The two-sided sleeve comprises an outside wall 30 comprising the bag body 12 and wall 20. It also comprises a lower side 32 defining open space 34 for insertion of the semi-rigid flexible support member 26 as illustrated in FIG. 4. The structural support member has a rounded shape approximately a semicircle when operatively associated with continuous wall 20 and bottom 18. The semi-rigid flexible support member 26 is made from suitable material for providing flexibility for opening the containment device 10 from a collapsed position 72 and an open position for supporting containment device 10 creating containment space 28. The structural support member 26 also must be sufficiently flexible to be compressed into a collapsed position 72 for storage in a container or package 74. Further, the material utilized in manufacturing the structural support member 26 must be an approved material that can withstand sterilization treatment of the containment device 10 prior to use. Many conventional materials, including various plastics may be utilized, however, polypropylene is preferred.

In addition, fluid containment device 10 may contain access ports 36 wherein one or more may be placed on the upper section of the bag body or in any other convenient location. The access ports 36 provide access to the body for the care provider and can be resealed. Zippers are illustrated. However, any conventional closure means is acceptable.

Fluid is drained or withdrawn from the bag body 12 by tube 38, which may have one or more extension tubes. The tubes enter the bag through port 40 at distal end 24. One tube 42 may enter the bag for collection of fluids that may drain through that area of the bag. Indeed, one or more perforated tubes 44 descending into the bag, preferably to the proximal end 23 or opening 22 for collection of fluids, may be utilized. It is preferred to have perforations 46 in the tubes for collecting fluids and tissue as they drain toward tube 42 and drain 48. Drain 48 includes a funnel device 50 having a set diameter 52 connected to hose 54. The large diameter 52 of the funnel and large diameter 56 of hose 54 allows for the insertion of tube 42 or perforated tube 44 therein, creating a double-walled tube 58. A vacuum pump (not shown) can be attached to double-walled tube 58 to remove liquid and biological tissue through perforated tube 44. Further, drain 48 may capture liquids and tissue as they collect in the bottom 18 of distal portion 24 of bag body 12. The funnel shaped device 50 assists in the collection of liquids and tissue. When vacuum is applied, it assists in the removal of liquids and tissue through hose 54 also, which is surrounding perforated tube 44, as well as through perforated tube 44.

An especially useful feature of the present invention is lower support 60, which is attached to bottom 18 in the lower section 14 of the fluid containment device 10 for elevating the limb of the patient at the proximal end 23 of the device. Support 60 runs the width of bottom 18. By elevating the limb, a gradient is created allowing gravity to assist the flow of irrigation fluids and tissue to the port 40 for removal from the bag. To assist in the removal of irrigation fluids and tissue from the bag, the tube 36 and perforated tubes 44 may be subjected to vacuum pressure.

Figure 5:
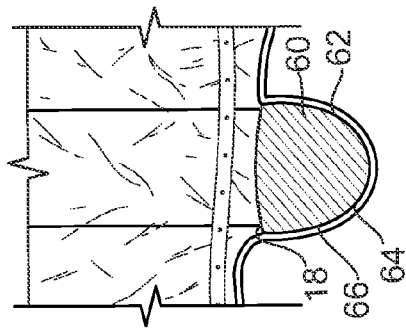
FIG. 5 is a cross-sectional view of a containment device taken along lines 5-5 of FIGS. 3 and 6.

Lower support 60 may be made from any lightweight, sturdy material, for example, polystyrene, that is fitted within sleeve 62 and the floor 18 of the fluid containment device 10 as shown in FIG. 5. Sleeve 62 has outer wall 64 defining open space 66 wherein lower support member 60 is inserted. Lower support 60 also provides comfort to the patient by providing support to the limb. Any suitable means for closing the device at its proximal end to secure the device to the patient's limb may be utilized. It is preferable, however, to use hook and loop fastening means 29 for convenience.

Referring to FIG. 1, fluid containment device 10 is shown in a collapsed or folded position 72. In position 72, the device may be stored for transportation. FIG. 7 shows a container or package 74 that has a flat bottom 76 and rounded surface wall 78 that matches the contour of the folded fluid containment device 10. More specifically, wall 78 matches the contour of the folded structural support members 26. The package 74 provides convenient, sterile and secure storage of fluid containment device 10 for transport. The folded position 72 of the containment device provides less space for transportation of sterile devices. In addition, package 74 may be used to transport a contaminated fluid containment device 10 with irrigation fluid and tissue for disposal. The combination of the containment device 10 and storage package 74 provides a convenient solution for proper handling and disposal of contaminated irrigation fluid and biological tissue.

Figure 2:
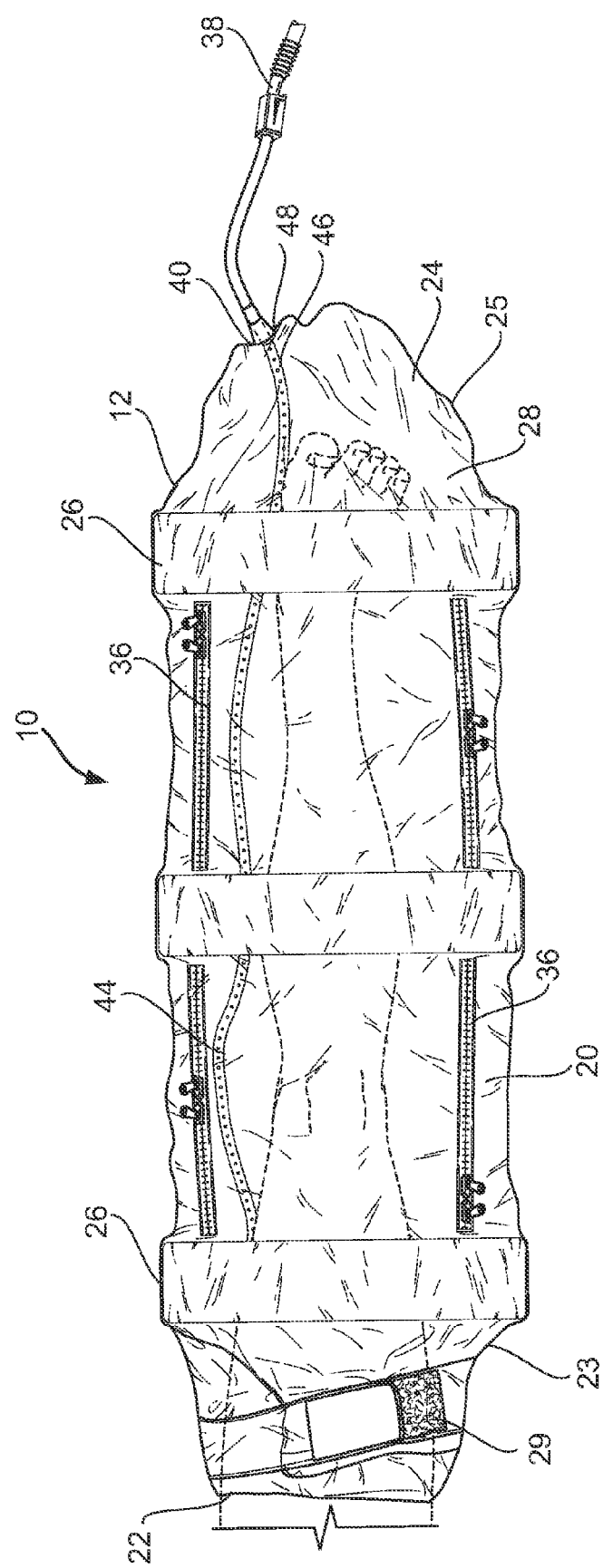
FIG. 2 is a top view of a fluid containment device surrounding a patient's leg.
Figure 3:
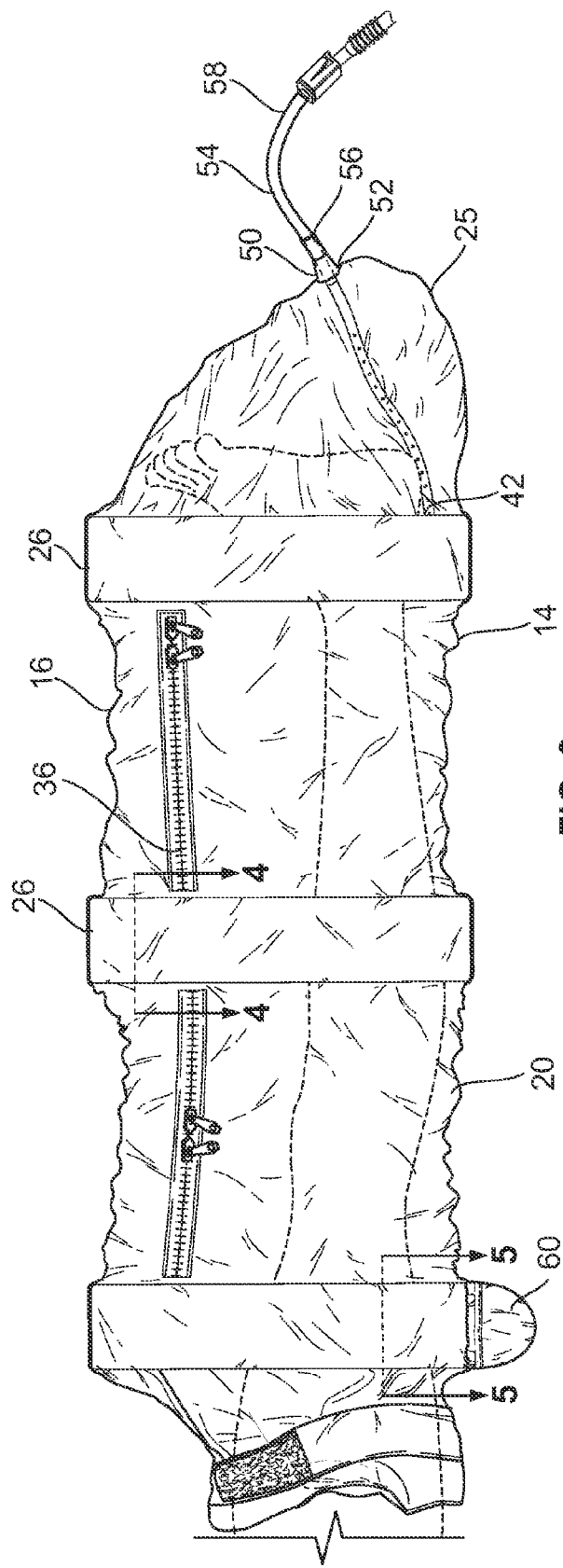
FIG. 3 is a cross-sectional side view of a fluid containment device showing that the proximal support is in a position that is elevated from the distal support to allow draining of fluids collected in the device.

FIG. 2 illustrates a top view of the fluid containment device 10 with a patient's leg inserted therein to illustrate perforated tubes 44 extending from the distal end of the bag body 12 to the proximal end 23 for the collection of fluids and other materials. Drain 48 is shown for collecting fluid at the distal portion 24 in bottom 18 of the bag because of the gradient created by the use of lower support 60 (not shown) at the proximal end 23 of the fluid containment device.

FIG. 6 illustrates a shorter version 11 of containment device 10 with two semi-rigid support members 26.

It should be apparent to those skilled in the art that various modifications and adaptation of the structure described above are possible without departing from the spirit of the invention, the scope of which is defined in the appended claims.

What is claimed is:

1. A collapsible, flexible fluid containment device comprising:
   (a) a flexible bag body defining a containment space;
   (b) said bag body comprising a wall having a proximal end, distal end, and drainage area at its distal end and double-walled sleeves;

(c) said wall including attached substantially semi-circular flexible structural support members positioned in the double-walled sleeves;

(d) an elevated lower support in a double-wall sleeve positioned under the proximal end to create a gradient so fluids will migrate to the drainage area at the distal end;

(e) means for accessing through said body bag and into said containment space;

(f) a port in the drainage area of the distal end of the bag for draining fluids; and (g) a flexible perforated tube placed inside the device and exiting the port for collecting and removing fluids and tissue from the device, wherein the proximal end and distal ends fold towards each other to collapse into a compact structure for storage and disposal.

2. The flexible fluid containment device according to claim 1, wherein the device has one or more tubes for collecting and removing fluids from the device.

3. The flexible fluid containment device according to claim 2, wherein the tubes may be subjected to vacuum pressure to assist in the removal of fluids.

4. The flexible fluid containment device according to claim 1, wherein a first single tube is integrated for removing fluids from the device.

5. The flexible fluid containment device according to claim 4, wherein the first tube is of a set diameter connected with the port for removing fluids from the device.

6. The flexible fluid containment device according to claim 5, wherein the perforated tube is placed inside the first tube to assist in the removal of fluids from the device and from the inside of the first tube of the device.

* * * * *